(12) United States Patent
Ataka et al.

(10) Patent No.: US 10,055,518 B2
(45) Date of Patent: Aug. 21, 2018

(54) APPARATUS AND METHOD FOR GENERATING SHAPE DATA

(71) Applicants: FUJITSU LIMITED, Kawasaki-shi, Kanagawa (JP); The University of Tokyo, Tokyo (JP)

(72) Inventors: Tadashi Ataka, Kawasaki (JP); Masahiro Watanabe, Kawasaki (JP); Satoshi Fuchikami, Fukuoka (JP); Yoshimasa Kadooka, Kawasaki (JP); Toshiaki Hisada, Tokyo (JP); Seiryo Sugiura, Tokyo (JP); Takumi Washio, Tokyo (JP); Jun-ichi Okada, Tokyo (JP)

(73) Assignees: FUJITSU LIMITED, Kawasaki (JP); The University of Tokyo, Tokyo (JP)

( * ) Notice: Subject to any disclaimer, the term of this patent is extended or adjusted under 35 U.S.C. 154(b) by 933 days.

(21) Appl. No.: 14/556,602

(22) Filed: Dec. 1, 2014

(65) Prior Publication Data
US 2015/0161297 A1 Jun. 11, 2015

(30) Foreign Application Priority Data
Dec. 5, 2013 (JP) .................. 2013-251693

(51) Int. Cl.
G06F 17/50 (2006.01)
G06T 17/20 (2006.01)
G16H 50/50 (2018.01)

(52) U.S. Cl.
CPC .......... G06F 17/5009 (2013.01); G06T 17/20 (2013.01); G16H 50/50 (2018.01);
(Continued)

(58) Field of Classification Search
CPC .......... G06T 17/20; G06T 2207/30101; G06T 2207/30104; G06F 19/34; G06F 17/5009; G06F 19/26; G06F 2217/34
See application file for complete search history.

(56) References Cited

U.S. PATENT DOCUMENTS

2005/0018885 A1* 1/2005 Chen ...................... G06T 17/00
382/128
2011/0306868 A1 12/2011 Nagao
2012/0041318 A1 2/2012 Taylor

FOREIGN PATENT DOCUMENTS

JP 2002-537008 11/2002
JP 2012-055621 3/2012
(Continued)

OTHER PUBLICATIONS

Zhang et al., "Patient-specific vascular NURBS modeling for isogeometric analysis of blood flow" (2007), Computer Method in Applied Mechanics and Engineering, vol. 196, Issues 29-30, pp. 2943-2959 [retrieved from https://www.sciencedirect.com/science/article/pii/S0045782507000801].*

(Continued)

Primary Examiner — Brian W Wathen
(74) Attorney, Agent, or Firm — Oblon, McClelland, Maier & Neustadt, L.L.P.

(57) ABSTRACT

A shape data generation apparatus includes a detection unit and a generation unit. With reference to model information indicating the thicknesses and the positions of both ends of a plurality of elements each having a cylindrical surface, the detection unit detects a connection point where two or more elements are connected to each other, on the basis of the positions of both ends of the elements. The generation unit generates a curved surface collectively covering the connecting ends of the two or more elements, on the basis of the (Continued)

thicknesses and the positions of both ends of the two or more elements connected at the connection point.

7 Claims, 20 Drawing Sheets

(52) U.S. Cl.
CPC .... *G06F 2217/16* (2013.01); *G06T 2207/30101* (2013.01); *G06T 2207/30104* (2013.01)

(56) References Cited

FOREIGN PATENT DOCUMENTS

| JP | 2013-534154 | 9/2013 |
|----|----|----|
| WO | WO 00/46689 A1 | 8/2000 |
| WO | WO 2010/098444 A1 | 9/2010 |

OTHER PUBLICATIONS

Guo et al., "Mesh quality oriented 3D geometric vascular modeling based on parallel transport frame" (Aug. 2013), Computers in Biology and Medicine, vol. 43, pp. 879-888 [retrieved from https://www.sciencedirect.com/science/article/pii/S0010482513000930].*
Office Action dated May 2, 2017 in Japanese Patent Application No. 2013-251693 (with English translation).
Takayuki Ohguchi, et al., "Bio-Design fora Microworld", Fujitsu, Fujitsu Limited, vol. 41, No. 2, Mar. 1990, pp. 121-141.

\* cited by examiner

110 CORONARY CIRCULATION MODEL STORAGE UNIT

111 NODE INFORMATION TABLE

| NODE NO. | COORDINATES |
|---|---|
| 1 | 0.00 0.00 0.00 |
| 2 | 0.00 0.00 0.50 |
| ⋮ | ⋮ |

112 BLOOD VESSEL ELEMENT INFORMATION TABLE

| ELEMENT NO. | NODES | RADIUS |
|---|---|---|
| 1 | 1,2 | 0.0030 |
| 2 | 2,3 | 0.0028 |
| ⋮ | ⋮ | ⋮ |

FIG. 5

[BEFORE ADDITION OF SURFACES COVERING BRANCH POINT]

[AFTER ADDITION OF SURFACES COVERING BRANCH POINT]

APPARATUS AND METHOD FOR GENERATING SHAPE DATA

CROSS-REFERENCE TO RELATED APPLICATION

This application is based upon and claims the benefit of priority of the prior Japanese Patent Application No. 2013-251693, filed on Dec. 5, 2013, the entire contents of which are incorporated herein by reference.

FIELD

The embodiments herein relate to an apparatus and method for generating shape data.

BACKGROUND

Numerical analysis using computer simulation is increasingly carried out in a variety of fields. For example, in the medical field, numerical analysis is carried out to reproduce a coronary circulation, which is a vascular network for delivering oxygen and so on to the heart. In such numerical analysis, the vascular network of the heart is represented by a three-dimensional coronary circulation model. For example, in the coronary circulation model, the vascular network is reproduced by connecting elements having radius information.

Further, for example, there is a technique of generating a three-dimensional model representing at least part of a patient's heart on the basis of the patient-specific data on the geometric shape of the heart. With this technique, a physics-based model relating to the characteristics of patient's blood flow is generated, and the fractional flow reserve within the patient's heart is measured on the basis of the above-mentioned three-dimensional model and the physics-based model.

Please see, for example, Japanese National Publication of International Patent Application No. 2013-534154.

A coronary circulation model may be displayed on a monitor for simulation. For example, a coronary circulation model of a patient's heart is displayed so as to confirm the state of the patient's heart.

However, in the case where the conventional techniques are used to display a coronary circulation model, joints between elements of blood vessel may look unnatural. That is to say, in the data of a coronary circulation model, data on each element of the blood vessels has information about length and radius, and therefore blood vessel elements are in cylindrical shape if they are displayed based on the data. Since the blood vessel elements are cylindrical, a blood vessel at a portion where the blood vessel branches into two looks unnatural because there is generated a gap at a connection portion connecting the thick main blood vessel and the two thin branch blood vessels. If the blood vessels in the displayed coronary circulation model look unnatural, it is difficult to visually identify an abnormal portion in the blood vessels, which is a problem.

In this connection, if a model of the vascular network of any other organ than the heart is approximately displayed with a combination of cylindrical elements, the model looks unnatural, like the coronary circulation model. This problem is not limited to the case of displaying a model representing a vascular network. That is to say, if a model is generated by approximating tubes, which are connected smoothly in nature, with a plurality of cylindrical elements having different radiuses and then is displayed, the model looks unnatural, which is a problem as in the case of displaying a coronary circulation model.

SUMMARY

According to one aspect, there is provided a shape data generation apparatus including a processor configured to execute a process that includes: detecting a connection point where two or more elements are connected to each other, based on positions of both ends of each of a plurality of elements, with reference to model information indicating thicknesses and the positions of the both ends of the plurality of elements each having a cylindrical surface; and generating a curved surface for collectively covering connecting ends of the two or more elements, based on the thicknesses and the positions of the both ends of the two or more elements connected at the connection point.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 5 illustrates an example of data structures in a coronary circulation model storage unit;

DESCRIPTION OF EMBODIMENTS

Figure 1:
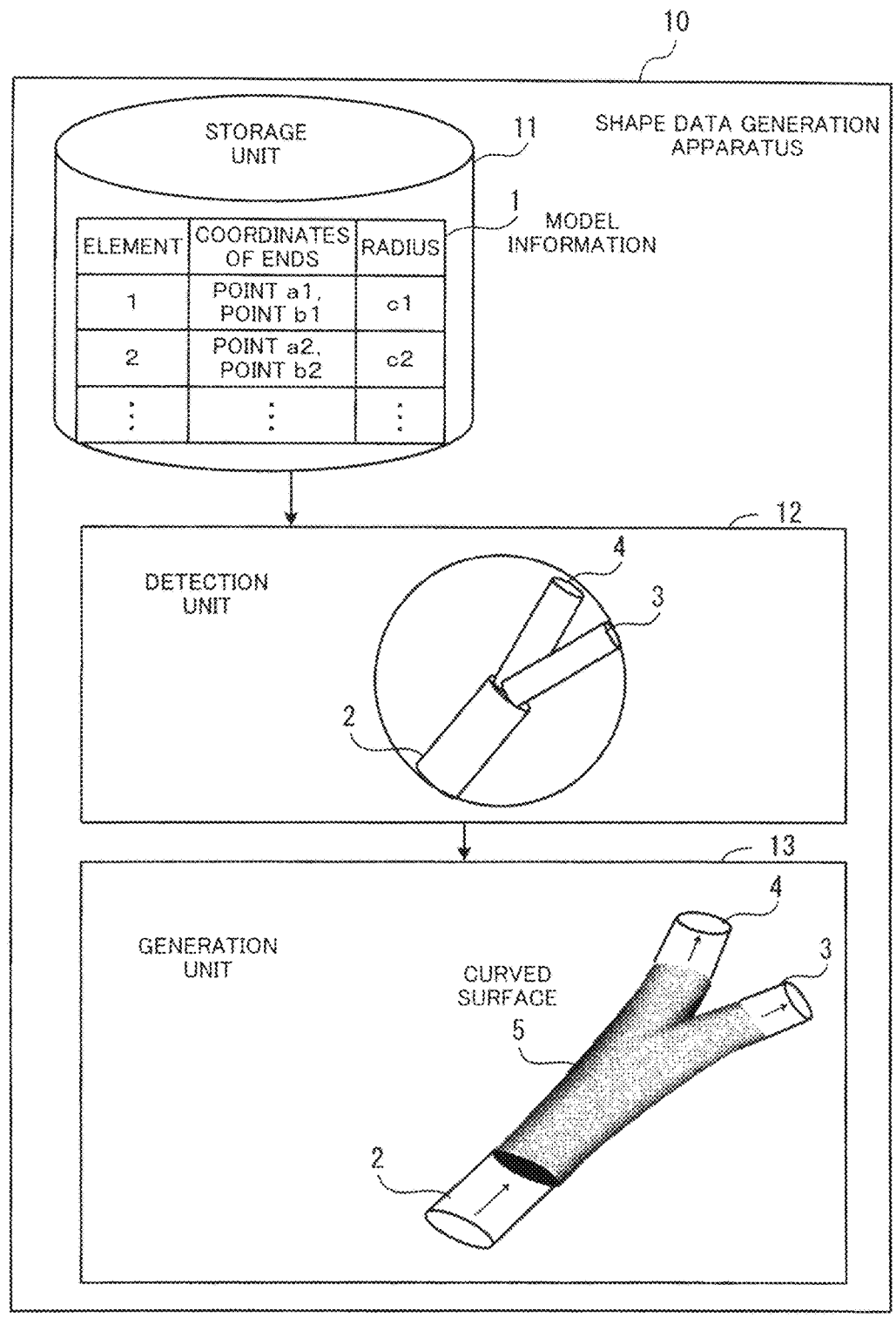
FIG. 1 illustrates an example of a functional configuration of a shape data generation apparatus according to a first embodiment.

Several embodiments will be described below with reference to the accompanying drawings, wherein like reference numerals refer to like elements throughout. Features of the embodiments may be combined unless they exclude each other.

First Embodiment

FIG. 1 illustrates an example of a functional configuration of a shape data generation apparatus according to a first embodiment. A shape data generation apparatus 10 includes a storage unit 11, a detection unit 12, and a generation unit 13.

The storage unit 11 stores therein model information 1 indicating the thickness and the positions of both ends for each of a plurality of elements each having a cylindrical surface. For example, for each of the elements, the coordinates of the end points and the radius of the element are indicated in the model information 1. A radius represents the thickness of an element. Instead of the radius, a diameter may be used in the model information 1.

The detection unit 12 detects a connection point where two or more elements 2 to 4 are connected to each other, on the basis of the positions of the both ends of the elements with reference to the model information 1 stored in the storage unit 11. For example, the detection unit 12 detects a plurality of elements 2 to 4 whose respective one ends have the same coordinates with reference to the model information 1. The position indicated by the same coordinates of the one ends of the plurality of detected elements 2 to 4 is the connection point where these elements 2 to 4 are connected to each other.

The generation unit 13 generates, for the two or more elements 2 to 4 connected at the connection point, a curved surface 5 that collectively covers the connecting ends of the elements 2 to 4, on the basis of the thicknesses and the positions of the both ends of the elements 2 to 4.

For example, in the case of a connection point where three elements are connected to each other, the generation unit 13 generates first to third curved surfaces which respectively cover the joints between two of the elements connected at the connection point. Taking the three connected elements as the first to third elements, the first curved surface covers a joint portion between the first and second elements, the second curved surface covers a joint portion between the first and third elements, and the third curved surface covers a joint portion between the second and third elements. The generation unit 13 then generates one or more curved surfaces that cover gaps between the first to third curved surfaces and the first to third elements. The generation unit 13 joins the generated curved surfaces to each other to thereby generate the smooth curved surface 5 covering the connecting ends of the elements 2 to 4.

As described above, the connection point is covered with the smooth curved surface 5. By doing so, when an area around the connection point is displayed on a screen, the plurality of elements is displayed as if these elements are connected by a smooth surface. For example, in the case where the elements 2 to 4 represent blood vessels, the displayed blood vessels look natural.

In this connection, the generation unit 13 may use, for example, Non-Uniform Rational B-Spline (NURBS) surfaces as surfaces forming the curved surface 5. The shape of a NURBS surface is defined by a plurality of control points. Therefore, the generation unit 13 sets, for example, at least one control point for defining the shape of the first curved surface, on each of the surface of the first element and the surface of the second element. In addition, the generation unit 13 sets at least one control point for defining the shape of the second curved surface, on each of the surface of the first element and the surface of the third element. The generation unit 13 also sets at least one control point for defining the shape of the third curved surface, on each of the surface of the second element and the surface of the third element. By determining an order of the control points such that NURBS surfaces are arranged on these control points, the generated NURBS surfaces get in contact with the surfaces of the elements 2 to 4.

In addition, to cover gaps, the generation unit generates one or more curved surfaces each of which shares one or more control points with any of the first to third curved surfaces and has a control point arranged on any surface of the first to third elements 2 to 4. By determining an order of the control points such that NURBS surfaces are arranged on these control points, each generated NURBS surface gets in contact with any of the first to third curved surfaces and the surfaces of the elements 2 to 4. As a result, the plurality of NURBS surfaces is joined smoothly and, in appearance, looks as one curved surface 5.

In addition, the generation unit 13 determines the positions of the control points such that the thickest element among the plurality of elements 2 to 4 is covered with the curved surface 5. For example, the generation unit 13 obtains the radius of the thickest element among the two or more elements connected at the connection point, and obtains two points that are away by a distance equal to the obtained radius from the connection point and are symmetrical about the connection point. These two points are set on, for example, a straight line orthogonal to a plane including the ends of the elements 2 to 4 opposite to their connecting ends. The generation unit 13 sets these two points as common control points to the first to third curved surfaces. As a result, the curved surface 5 that covers the plurality of elements 2 to 4 without fail is generated.

In this connection, if the length of an element connected at the connection point is shorter than the thickness thereof, the generation unit 13 generates the curved surface 5 such as not to entirely cover the element. For example, in the case where the length of an element is longer than a value obtained by multiplying the radius thereof by a predetermined value, the generation unit 13 defines a plane orthogonal to a line segment connecting the both ends of the element, at a position that is away by a distance of predetermined times longer than the radius from the connection point, on the line segment. In the case where the length of the element is shorter than or equal to the value obtained by multiplying the radius thereof by the predetermined value, on the other hand, the generation unit defines a plane orthogonal to the line segment connecting the both ends of the element, at a position that is away by a distance shorter than the length of the element from the connection point, on the line segment. Then, the generation unit 13 sets control points for defining the shape of a curved surface, on the generated plane. This prevents the curved surface 5 from entirely covering the element connected at the connection point even in the case where the length of the element is shorter than the thickness thereof.

It is noted that the detection unit 12 and the generation unit 13 may be implemented by using, for example, a processor provided in the shape data generation apparatus 10. The storage unit 11 may be implemented by using, for example, a memory provided in the shape data generation apparatus 10. In addition, lines connecting units, illustrated in FIG. 1, represent part of communication paths, and other communication paths than illustrated may be set.

Second Embodiment

The following describes a second embodiment. The second embodiment is to display a coronary circulation model, which is to be used for simulating the heart's coronary circulation, such that the coronary circulation model looks biologically natural. For example, by using a high performance computer, it is possible to model the blood vessel structure of the heart's coronary circulation of a patient and to simulate blood flows and so on. Through this simulation, an abnormality in the blood flows or the like may be detected. If detecting an abnormality, a doctor is able to investigate the cause of the abnormality by confirming the arrangement of the blood vessels and so on in the detailed areas of the coronary circulation model. If the detailed areas of the displayed coronary circulation model look biologically unnatural, the doctor feels discomfort with the model as a whole and may fail to find an unnatural arrangement of blood vessels that may be the cause of the abnormality. To deal with this, the second embodiment is intended to cover the branch portions of blood vessels in a coronary circulation model with curved surfaces in order to display the blood vessels such as to look biologically natural.

Figure 2:
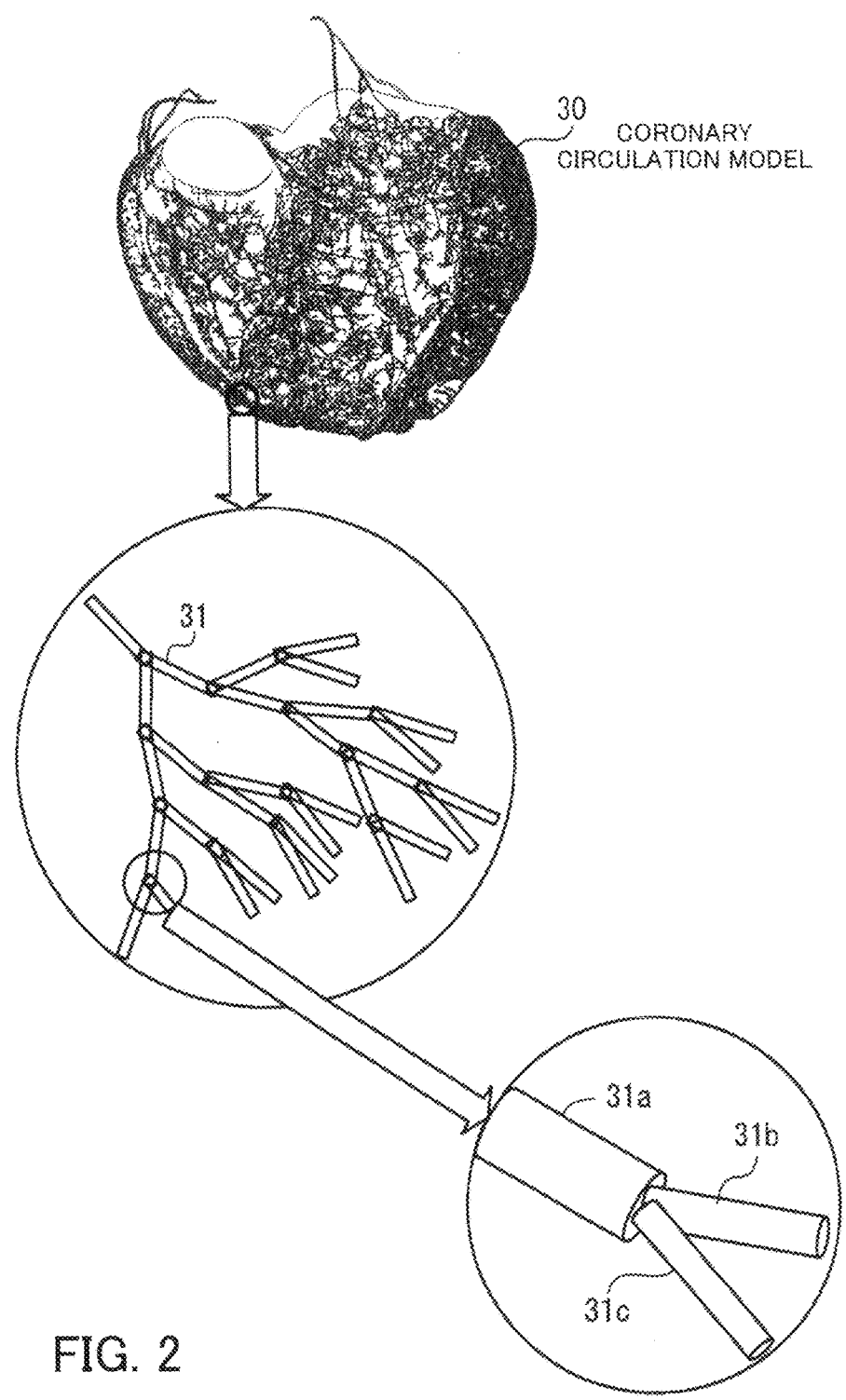
FIG. 2 illustrates an example of a coronary circulation model.

FIG. 2 illustrates an example of a coronary circulation model. A coronary circulation model 30 is a three-dimensional model reproducing the arteries and veins of a heart. It is possible to reproduce even, for example, capillaries in the coronary circulation model 30. In the vascular network represented by the coronary circulation model 30, there are many branches from, for example, the main artery and the main vein. A blood vessel gradually becomes thinner each time it branches. In the coronary circulation model 30, the branch points of blood vessels are defined as nodes, and a portion between two nodes is taken as one blood vessel element 31.

In the coronary circulation model 30, the cylindrical shape of the blood vessel element 31 is defined by the position of the both ends and the radius thereof. Each blood vessel element 31 is cylindrical. Therefore, at a branch point where a single thick blood vessel element 31a branches into two blood vessel elements 31b and 31c, the blood vessel elements are not connected smoothly. Therefore, if the coronary circulation model 30 is displayed in enlargement as it is, the blood vessels at branch points look unnatural. In this connection, the branch points are one example of the connection point explained in the first embodiment.

To deal with this, in the second embodiment, smooth surfaces are generated to cover branch points using NURBS surfaces when a coronary circulation model is displayed using a computer. This makes it possible to display the blood vessels around branch points without any of biological strangeness.

Figure 3:
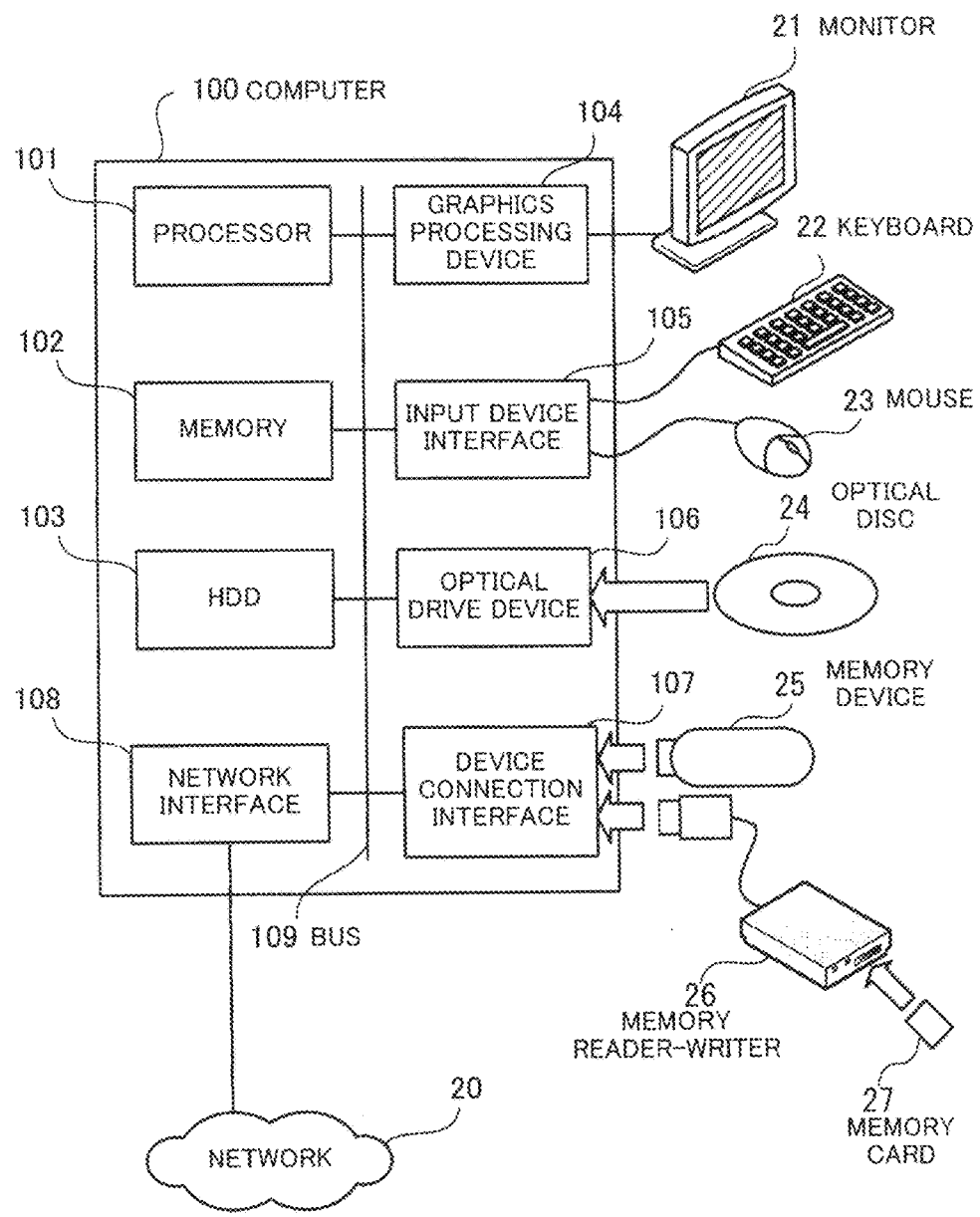
FIG. 3 illustrates an example of a hardware configuration of a computer to be used in the second embodiment.

FIG. 3 illustrates an example of a hardware configuration of a computer to be used in the second embodiment. A computer 100 is entirely controlled by a processor 101. To the processor 101, a memory 102 and peripherals are connected with a bus 109. The processor 101 may be a multi-processor. The processor 101 may be, for example, a Central Processing Unit (CPU), a Micro Processing Unit (MPU), or a Digital Signal Processor (DSP). Some or all of the functions of the processor 101 may be implemented by using an Application Specific Integrated Circuit (ASIC), Programmable Logic Device (PLD), or other electronic circuits.

The memory 102 is used as a main storage device of the computer 100. The memory 102 temporarily stores therein at least part of Operating System (OS) programs and application programs to be executed by the processor 101. The memory 102 also stores therein various kinds of data to be used while the processor 101 operates. As the memory 102, for example, a Random Access Memory (RAM) or another volatile semiconductor storage device may be used.

The peripherals connected to the bus 109 include a Hard Disk Drive (HDD) 103, a graphics processing device 104, an input device interface 105, an optical drive device 106, a device connection interface 107, and a network interface 108.

The HDD 103 magnetically writes and reads data on a built-in disk. The HDD 103 is used as an auxiliary storage device of the computer 100. The HDD 103 stores therein the OS programs, application programs, and various kinds of data. As the auxiliary storage device, a flash memory or another non-volatile semiconductor storage device may be used.

To the graphics processing device 104, a monitor 21 is connected. The graphics processing device 104 displays images on the screen of the monitor 21 in accordance with instructions from the processor 101. As the monitor 21, a display device using a Cathode Ray Tube (CRT), a liquid crystal display device, or the like may be used.

To the input device interface 105, a keyboard 22 and a mouse 23 may be connected. The input device interface 105 transfers signals from the keyboard 22 and mouse 23 to the processor 101. In this connection, the mouse 23 is an example of a pointing device, and another pointing device may be used. Other pointing devices include a touch panel, a tablet, a touchpad, a track ball, and so on.

The optical drive device 106 reads data from an optical disc 24 with laser light or the like. The optical disc 24 is a portable recording medium on which data is recorded so as to be read with reflection of light. The optical disc 24 may be a Digital Versatile Disc (DVD), DVD-RAM, Compact Disc Read Only Memory (CD-ROM), CD-R (Recordable), CD-RW (ReWritable), or the like.

The device connection interface 107 is a communication interface that allows peripherals to be connected to the computer 100. For example, a memory device 25 and a memory reader-writer 26 may be connected to the device connection interface 107. The memory device 25 is a recording medium provided with a function of communicating with the device connection interface 107. The memory reader-writer 26 is a device that writes and reads data on a memory card 27, which is a card type recording medium.

The network interface 108 is connected to a network 20. The network interface 108 communicates data with another computer or communication device over the network 20.

With the above hardware configuration, the processing functions of the second embodiment may be implemented. In this connection, the shape data generation apparatus 10 described in the first embodiment may be configured with the same hardware as the computer 100 of FIG. 2.

For example, the computer 100 realizes the processing functions of the second embodiment by executing a program stored in a computer-readable recording medium. The program describing the contents of processing to be executed by the computer 100 may be recorded on various types of recording media. For example, the program to be executed by the computer 100 may be stored on the HDD 103. The processor 101 loads at least part of the program from the HDD 103 to the memory 102 and then executes the program. Alternatively, the program to be executed by the computer 100 may be recorded on a portable recording medium, such as the optical disc 24, the memory device 25, the memory card 27, etc. By being installed on the HDD 103 under the control of the processor 101, for example, the program recorded on the portable recording medium become executable. Alternatively, the processor 101 may execute the program while reading the program directly from the portable recording medium.

The following describes the function of a computer 100 for displaying a coronary circulation model.

Figure 4:
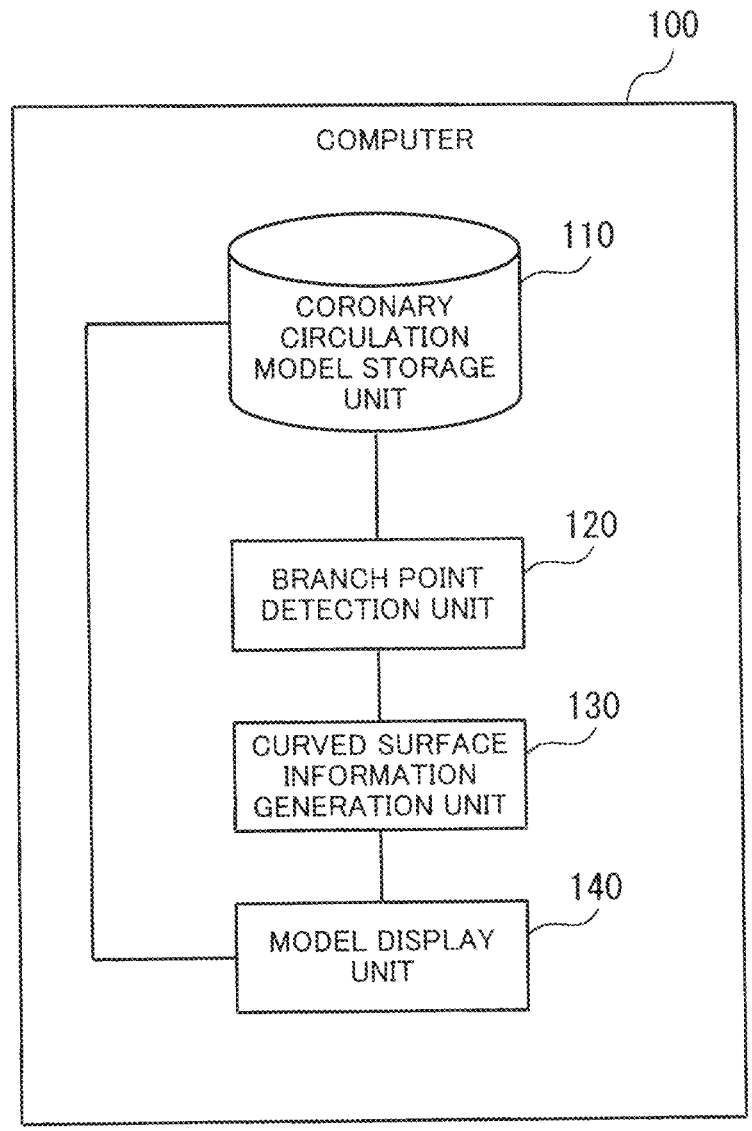
FIG. 4 is a block diagram illustrating the function of displaying a coronary circulation model.

FIG. 4 is a block diagram illustrating the function of displaying a coronary circulation model. To display a coronary circulation model 30, the computer 100 includes a coronary circulation model storage unit 110, a branch point detection unit 120, a curved surface information generation unit 130, and a model display unit 140.

The coronary circulation model storage unit 110 stores therein data representing the coronary circulation model 30. For example, a partial storage area of the memory 102 or HDD 103 may be used as the coronary circulation model storage unit 110.

The branch point detection unit 120 detects the branch points of blood vessels in a coronary circulation. For example, the branch point detection unit 120 detects, as a branch point, a point serving as all of the end point of one blood vessel element and the start points of a plurality of other blood vessel elements.

The curved surface information generation unit 130 generates information indicating curved surfaces that cover branch points. For example, for covering one branch point, the curved surface information generation unit 130 generates information that defines the shapes of six NURBS surfaces. When generating information on NURBS surfaces, the curved surface information generation unit 130 determines, for example, the positions of control points to be used for defining the shapes of the NURBS surfaces.

The model display unit 140 displays the coronary circulation model 30 having the branch points of the blood vessels covered with curved surfaces, on the monitor 21. For example, in response to user inputs, the model display unit 140 may enlarge or shrink the displayed coronary circulation model 30.

In this connection, lines connecting units, illustrated in FIG. 4, represent part of communication paths, and other communication paths than illustrated may be set. In addition, the functions of the units illustrated in FIG. 4 may be realized by, for example, the computer 100 executing program modules corresponding to the respective units.

Of the units illustrated in FIG. 4, the coronary circulation model storage unit 110, the branch point detection unit 120, and the curved surface information generation unit 130 are examples of the storage unit 11, the detection unit 12, and the generation unit 13 of the first embodiment illustrated in FIG. 1, respectively.

The following describes data structures used in the coronary circulation model storage unit 110.

FIG. 5 illustrates an example of data structures used in a coronary circulation model storage unit. The coronary circulation model storage unit 110 stores therein a node information table 111 and a blood vessel element information table 112.

The node information table 111 contains a node number (No.) and coordinates for each node. The node number is the identification number of the node. The coordinates are the coordinates of the node in three-dimensional space displaying a coronary circulation model 30.

The blood vessel element information table 112 contains an element number (No.), nodes, and a radius for each blood vessel element. The element number is the identification number of the blood vessel element. The nodes are expressed using the identification numbers of nodes at the both ends of the blood vessel element. The radius is the radius of the blood vessel element.

The following describes how to define the shape of a NURBS surface that is generated at a branch point of a blood vessel.

When placing a surface using NURBS, three parameters, i.e., the number of control points, the number of knots, and the number of orders, are used. A coronary circulation has more blood vessel elements than the other organs, and also has a great number of branch points. To reduce the number of polygons generated, these parameters, i.e., the number of control points, the number of knots, and the number of orders, are fixed. Since surfaces are generated, parametric equations for defining a NURBS surface, which is a parametric curved surface, use two parameters u and v. The number of control points indicates how many control points are arranged in each of the u direction and the v direction (a direction in which u, v increases). For example, the number of control points is set to three, meaning that three control points are arranged in each of the u direction and the v direction. In this case, the total number of control points is calculated as 9 (=3×3). In addition, the minimum number of knots and the minimum number of orders to generate a surface in the three dimensional space are set.

Surfaces to be arranged at a branch point are classified into surfaces to cover joint portions and connection surfaces to cover gaps between the surfaces and cylindrical blood vessel elements. For example, a joint portion is covered with a curved rhombic surface. In addition, as a connection surface, a curved trapezoid surface is used, for example.

For generating NURBS surfaces to be arranged at a branch point, the above-described parameters, i.e., the number of control points, the number of knots, and the number of orders, are fixed. Then, the coordinates of control points for defining the NURBS surfaces to be arranged are determined. Input information indicates only the coordinates of the nodes and radius of each line segment, and appropriate control points are arranged on the basis of the input information. The details of the parameters and the arrangement method will be described below.

Figure 6:
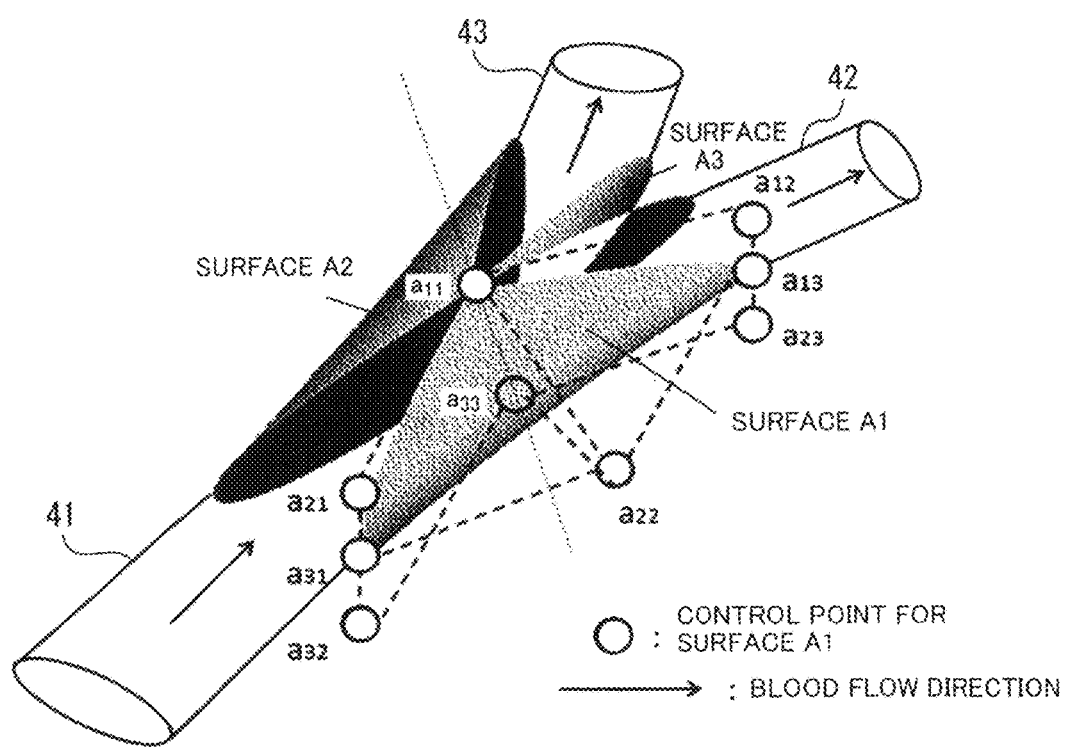
FIG. 6 illustrates an example of surfaces covering joint portions.

FIG. 6 illustrates an example of surfaces covering joint portions. In the example of FIG. 6, it is assumed that a blood vessel branches into two at a certain point in a coronary circulation. That is to say, an artery blood vessel element 41 branches into two branch vessel elements 42 and 43. Blood flows through the blood vessel element 41 toward the blood vessel elements 42 and 43. There are three joint portions at the branch point: a joint between the blood vessel element 41 and the blood vessel element 42; a joint between the blood vessel element 41 and the blood vessel element 43, and a joint between the blood vessel element 42 and the blood vessel element 43. Therefore, three surfaces are generated to cover these joint portions.

It is now assumed that a surface that covers the joint between the blood vessel elements 41 and 42 is taken as a surface A1, a surface that covers the joint between the blood vessel elements 41 and 43 is taken as a surface A2, and a surface that covers the joint between the blood vessel elements 42 and 43 is taken as a surface A3.

As an example, the following describes the surface A1 among the NURBS surfaces at these three joint portions. Nine control points are set for the surface A1. The identifiers of these control points are $a_{11}$, $a_{12}$, $a_{13}$, $a_{21}$, $a_{22}$, $a_{23}$, $a_{31}$, $a_{32}$, and $a_{33}$. The surface A1 has an outline defined by four control points $a_{11}$, $a_{13}$, $a_{22}$, and $a_{31}$, and is curved so as to cover the blood vessel elements 41 and 42. The two control points $a_{11}$ and $a_{13}$ on the outline of the surface A1 are arranged on the surfaces of the elements 41 and 42, respectively. Therefore, the surface A1 is in contact with the surfaces of the elements 41 and 42.

The left suffixes given to control points indicate the order of the control points arranged in the u direction on the NURBS surface, which is a parametric curved surface, and the right suffixes indicate the order of the control points arranged in the v direction on the NURBS surface.

Figure 7:
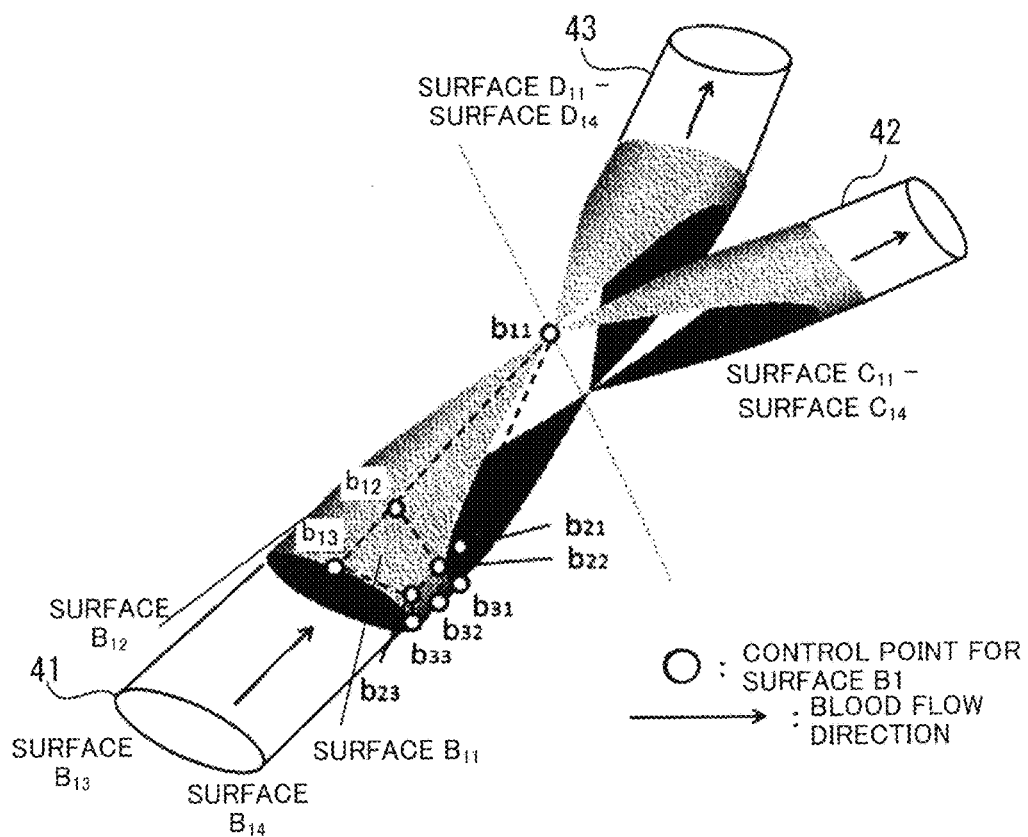
FIG. 7 illustrates an example of connection surfaces.

FIG. 7 illustrates an example of connection surfaces. Four connection surfaces are generated for each of the blood vessel elements 41 to 43. For example, four surfaces $B_{11}$, $B_{12}$, $B_{13}$, and $B_{14}$ are generated for the blood vessel element 41. Each surface is defined by nine control points. For example, control points $b_{11}$, $b_{12}$, $b_{13}$, $b_{21}$, $b_{22}$, $b_{23}$, $b_{31}$, $b_{32}$, and $b_{33}$ are set for the surface $B_{11}$. Similarly, four surfaces $C_{11}$, $C_{12}$, $C_{13}$, and $C_{14}$ are generated for the blood vessel element 42, and four surfaces $D_{11}$, $D_{12}$, $D_{13}$, and $D_{14}$ are generated for the blood vessel element 43.

Figure 8:
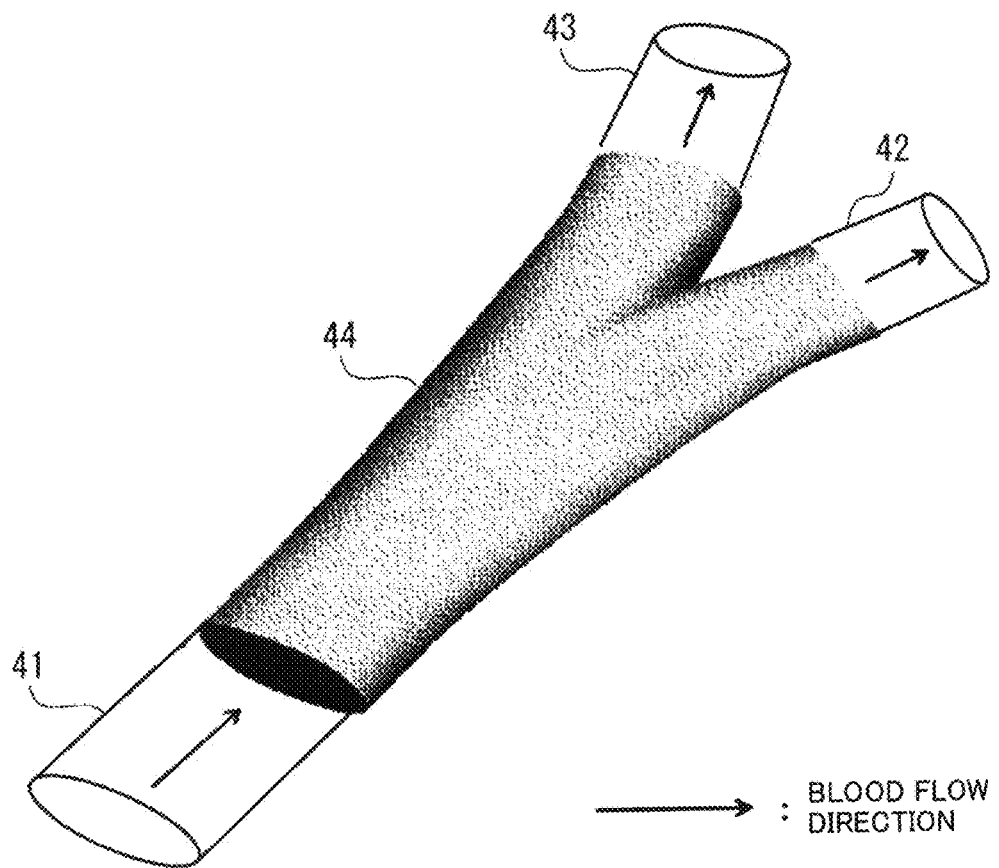
FIG. 8 illustrates an example of a branch point covered with generated surfaces.

FIG. 8 illustrates an example of a branch point covered with generated surfaces. When joined to each other, a plurality of generated surfaces look, in appearance, as one curved surface 44 covering the vicinity of a branch point. A blood vessel at the branch point, when covered with the curved surface 44, looks natural.

The following describes in detail how to determine control points for a NURBS surface. First, the method of determining control points for a surface that covers a joint portion will be described with reference to FIGS. 9 and 10.

Figure 9:
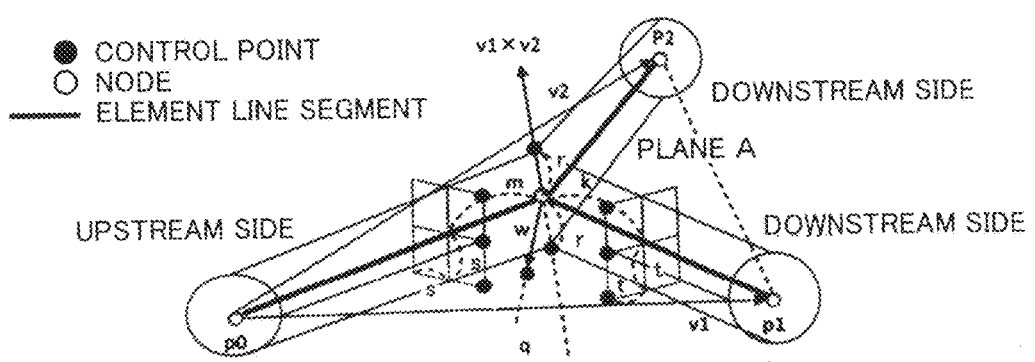
FIG. 9 illustrates an example of control points for a surface that covers a joint portion.
Figure 10:
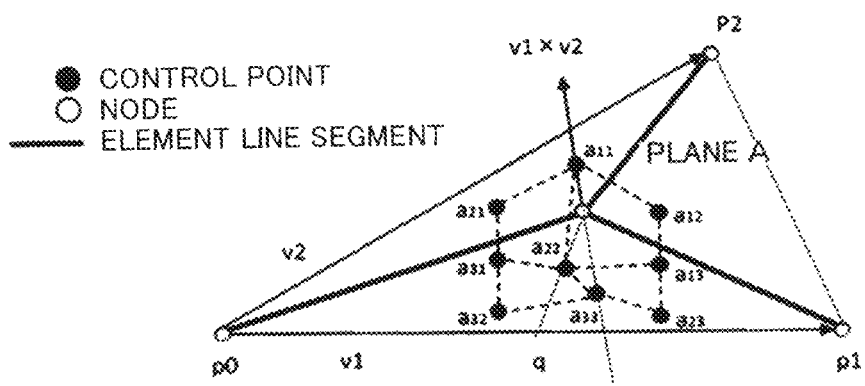
FIG. 10 illustrates an order of the control points for the surface that covers the joint portion.

FIG. 9 illustrates an example of control points for a surface that covers a joint portion. FIG. 9 illustrates control points for the surface A1 that covers the joint between the blood vessel elements 41 and 42. FIG. 10 illustrates an order of the control points for the surface that covers the joint portion. In FIGS. 9 and 10, control points are represented by black circles, nodes representing the both ends of the blood vessel elements 41 to 43 are represented by white circles, and line segments (element line segments) connecting the nodes representing the both ends of the individual blood vessel elements 41 to 43 are represented by thick lines.

It is assumed that the start point of the upstream blood vessel element 41 connected to the branch point is $p_0$, and the two end points of the downstream blood vessel elements 42 and 43 are $p_1$ and $p_2$. Now consider a plane A including these three points. The curved surface information generation unit 130 determines two points that are away by r (r is a positive real number) from the branch point, orthogonally to the plane A, and takes them as control points. The branch point serves as the end point of the blood vessel element 41 and also as the start points of the blood vessel elements 42 and 43.

r is a value of the maximum radius among the blood vessel elements 41 to 43 connected to the branch point. A NURBS surface is determined depending on the order of control points. Therefore, the curved surface information generation unit 130 determines identifiers indicating the order of the control points, and stores them in the memory 102. For example, the curved surface generation unit 130 takes a vector from the point $p_0$ to the point $p_1$ as a vector v1, and takes a vector from the point $p_0$ to the point $p_2$ as a vector v2. Then, the curved surface information generation unit 130 gives an identifier $a_{11}$ to a control point in the direction of the cross product of the vectors v1 and v2, of the two control points away by r from the branch point, and gives an identifier $a_{33}$ to a control point in its opposite direction.

Then, the curved surface information generation unit 130 arranges control points between joints. For example, the curved surface information generation unit 130 generates an upstream vector from the branch point toward the start point of the upstream blood vessel element 41 and a downstream vector from the branch point toward the end point of the downstream blood vessel element 42. Then, the curved surface information generation unit 130 normalizes the upstream vector and the downstream vector with the start point fixed at the branch point. The normalization is a process of converting the length of a vector into a unit vector whose length is 1. The curved surface information generation unit 130 obtains a line segment connecting the end points of the normalized upstream and downstream vectors. The curved surface information generation unit 130 further generates a vector w of length 2r from the branch point in the q direction, with the middle point of the obtained line segment taken as q. The generated vector w is a vector having a direction that divides an angle between the upstream vector and the downstream vector into halves. Then, the curved information generation unit 130 takes the end point of the vector w as a control point and gives an identifier $a_{22}$ to this control point. By arranging the control point in a direction that divides the angle between the upstream vector and the downstream vector into halves as described above, it is possible to arrange the control point at the appropriate position, irrespective of the lengths of the blood vessel elements 41 and 42 connected.

Further, the curved surface information generation unit 130 arranges remaining control points. For example, the curved surface information generation unit 130 generates a vector of length m (m is a positive real number) from the branch point in the $p_0$ direction. Then, the curved surface information generation unit 130 generates a square with each side of 2s (s is a positive real number) in length, using the generated vector as a normal line and the end point of the vector as a center, and obtains the vertices and the middle point of each side of the generated square. s is the radius of the upstream blood vessel element 41. Two sides of the generated square are orthogonal to the direction of the cross product of the vectors v1 and v2 (see FIG. 9).

There are eight points in total: the vertices and the middle points of the sides of the generated square. Of these points, the curved surface information generation unit 130 takes three points that are closer to the joint as control points, and gives identifiers $a_{21}$, $a_{31}$, and $a_{32}$ to these control points, in order from the one closest to $a_{11}$. In this connection, the control point $a_{31}$ is arranged on the surface of the blood vessel element 41.

Similarly, the curved information generation unit 130 generates a vector having a length of k (k is a positive real number) from the branch point in a direction to the end point $p_1$ of the downstream element. Then, the curved surface information generation unit 130 generates a square with each side of 2t (t is a positive real number) in length, using the generated vector as a normal line and the end point of the vector as a center, and obtains the vertices and the middle point of each side of the square. t is the radius of the downstream blood vessel element 42. Two sides of the generated square are orthogonal to the direction of the cross product of the vectors v1 and v2 (see FIG. 9).

There are eight points in total: the vertices and the middle points of the sides of the generated square. Of these points, the curved surface information generation unit 130 takes three points that are closer to the joint as control points, and gives identifiers $a_{12}$, $a_{13}$, and $a_{23}$ to the control points, in order from the one closest to $a_{11}$. In this connection, the control point $a_{13}$ is arranged on the surface of the blood vessel element 42.

In the way described above, the control points for a NURBS surface at a joint portion are arranged. After control points are arranged for the remaining two joints in the same way, the arrangement of control points for the joint portions is completed.

Figure 11:
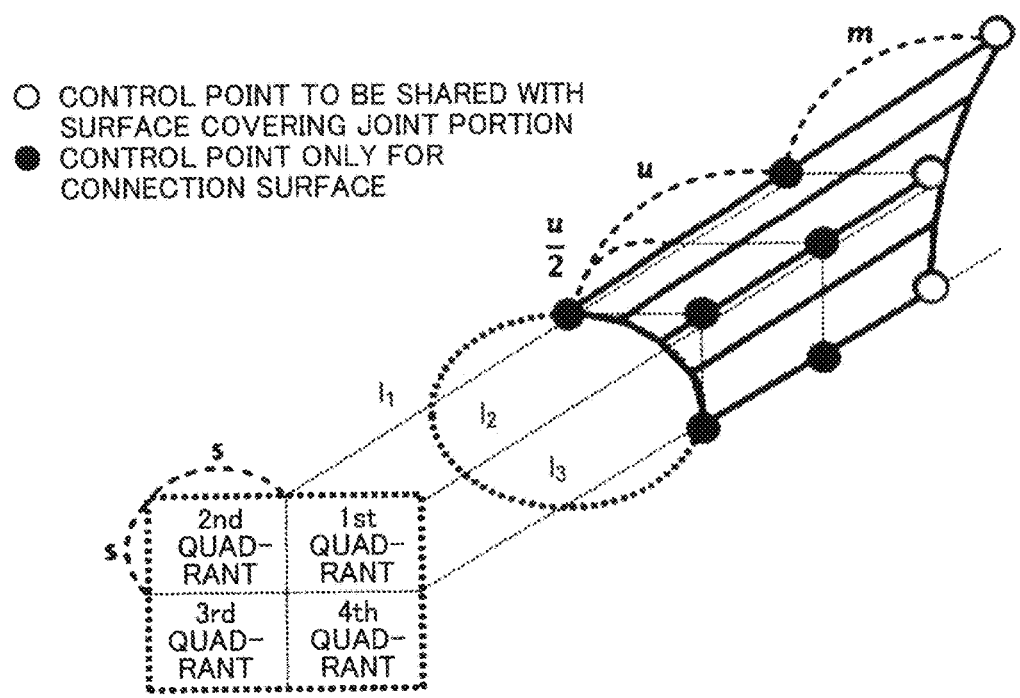
FIG. 11 is a first diagram illustrating an example of control points for a connection surface.
Figure 12:
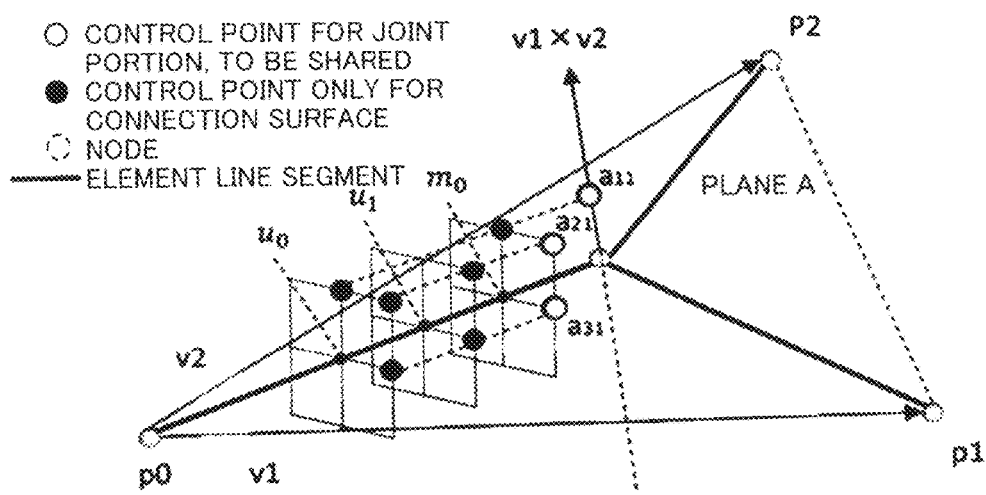
FIG. 12 is a second diagram illustrating an example of control points for a connection surface.

A method of determining control points for connection surfaces will be described with reference to FIGS. 11 and 12. FIG. 11 is a first diagram illustrating an example of control points for a connection surface. FIG. 12 is a second diagram illustrating an example of control points for a connection surface.

The curved surface information generation unit 130 arranges control points for NURBS surfaces that smoothly connect the surfaces covering the joint portions and the cylindrical surfaces of the blood vessel elements 41 to 43, as the control points for connection surfaces. For example, the curved surface information generation unit 130 matches a border of a connection surface and a border of a surface covering a joint portion to each other. To this end, the curved surface information generation unit 130 uses control points for the surface covering the joint portion, also as control points for the border portion between the connection surface and the surface covering the joint portion out of control points for the connection surface. Referring to FIGS. 11 and 12, control points shared with the surface covering the joint portion are represented by white circles, and control points used only for the connection surface are represented by black circles.

By using the same control points for both the surface covering the joint portion and the connection surface as described above, no gap is generated in the border between these surfaces. The surface covering the joint portion and the connection surface may be connected to each other discontinuously. However, after being subjected to a shading process, these surfaces, when displayed, look connected to each other smoothly, without giving a viewing user any sense of strangeness.

A connection surface is formed of surfaces obtained by dividing a surface orthogonal to the line segment connecting the ends of each blood vessel element into quadrants (see FIG. 11). More specifically, the curved surface information generation unit 130 generates four connection surfaces corresponding to the respective first to fourth quadrants around the blood vessel element 41. Similarly, the curved surface information generation unit 130 generates four connection surfaces around each of the blood vessel elements 42 and 43.

Now consider the connection surfaces around the blood vessel element 41 on the upstream side of the branch point. The following describes how to determine control points for one connection surface $B_{11}$ among four connection surfaces $B_{11}$, $B_{12}$, $B_{13}$, and $B_{14}$ (see FIG. 7) generated around the blood vessel element 41.

First, the curved surface information generation unit 130 determines that the control points $a_{11}$, $a_{21}$, and $a_{31}$ for the surface A1 covering the joint portion are to be shared as control points for the connection surface $B_{11}$. Then, the curved surface information generation unit 130 takes a point away by m from the branch point to the upstream direction as $m_0$, and takes points away by u and u/2 (u is a positive real number) from $m_0$ as $u_0$ and $u_1$, respectively. At this time, the curved surface information generation unit 130 defines squares that are orthogonal to the line segment and have each side of 2s in length, using the points $m_0$, $u_0$, and $u_1$ as centers. There are eight points in total: the vertices and the middle points of the sides of a defined square. Then, the curved surface information generation unit 130 takes, as control points, points belonging to a quadrant in question (first quadrant in the example of FIGS. 11 and 12) among the eight points of the square (including points on borders between quadrants).

Further, the curved surface information generation unit 130 defines three straight lines that are parallel to the line segment connecting the both end nodes of the blood vessel element and pass through the control points $a_{11}$, $a_{21}$ and $a_{31}$, respectively. Of these straight lines, a straight line passing through the control point $a_{11}$ is taken as $l_1$, a straight line passing through the control point $a_{21}$ is taken as $l_2$, and a straight line passing through the control point $a_{31}$ is taken as $l_3$. Then, the curved surface information generation unit 130 excludes a point on the straight line $l_1$ among the points of the square having the center $u_1$ from the control points.

Then, the curved surface information generation unit 130 gives identifiers to the nine control points. For example, the curved surface information generation unit 130 gives the control points exiting on the straight line 1, (i=1, 2, 3) identifiers $b_{ij}$ (j=1, 2, 3) in order from the one closest to the branch point. For example, the control points on the straight line $l_1$ for the connection surface $B_{11}$ on the upstream side are given identifiers $b_{11}$, $b_{12}$, and $b_{13}$ in order the control points appear in the upstream direction.

Similarly, the curved surface information generation unit 130 arranges control points for the other three connection surfaces on the upstream side. In addition, the curved surface information generation unit 130 arranges control points for connection surfaces around the downstream blood vessel elements.

The control points are arranged for each branch point in the way described above. Since there are a great number of branch points in the blood vessels of the coronary circulation model 30, it is preferable that control points are arranged as efficient as possible. Therefore, for the coronary circulation model 30, control points are automatically arranged in the following manner.

The coronary circulation model 30 is described, for example, in line arguments of the Unstructured Cell Data (UCD) format. As illustrated in FIG. 2, in the coronary circulation model 30, the coordinates of the start and end points of all blood vessel elements are described together with unique node numbers, and each of the blood vessel elements is assigned a unique element number. Information on combinations of node numbers of nodes defining blood vessel elements includes radius information. Therefore, by referring to the data of the coronary circulation model 30, all blood vessel elements extending from a node serving as a branch point are obtained.

To this end, the curved surface information generation unit 130 classifies control points into node-based control points and element-based control points. Then, the curved surface information generation unit 130 obtains node-based control point candidates and element-based control point candidates independently, and appropriately combines these candidates as control points for NURBS surfaces. Collectively extracting control point candidates in advance streamline a process for calculating the positions of the control points, and so on. In addition, for example, the curved surface information generation unit 130 assigns regular numbers to the obtained control pints. This makes it easier to determine combinations of control point candidates as the control points for the NURBS surfaces.

Figure 13:
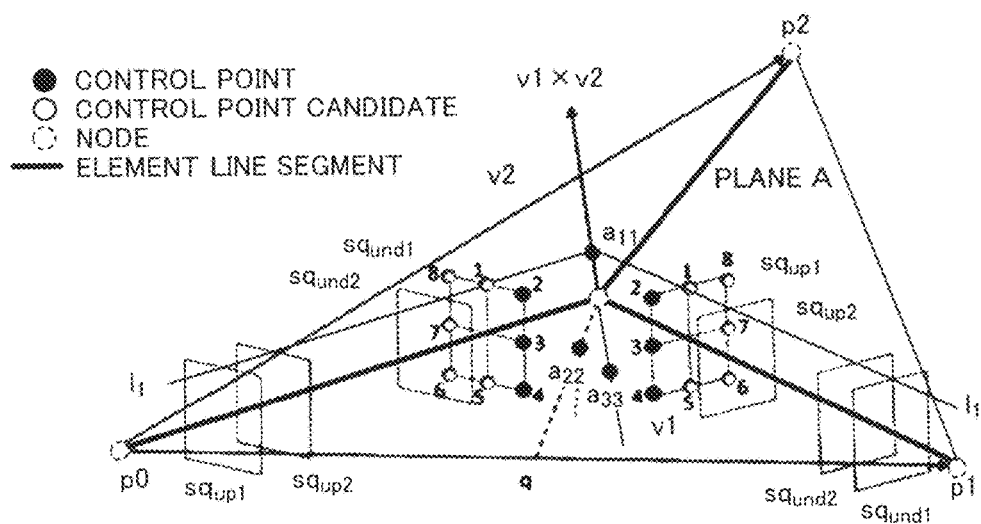
FIG. 13 illustrates an example of combining control points for surfaces covering a joint.
Figure 14:
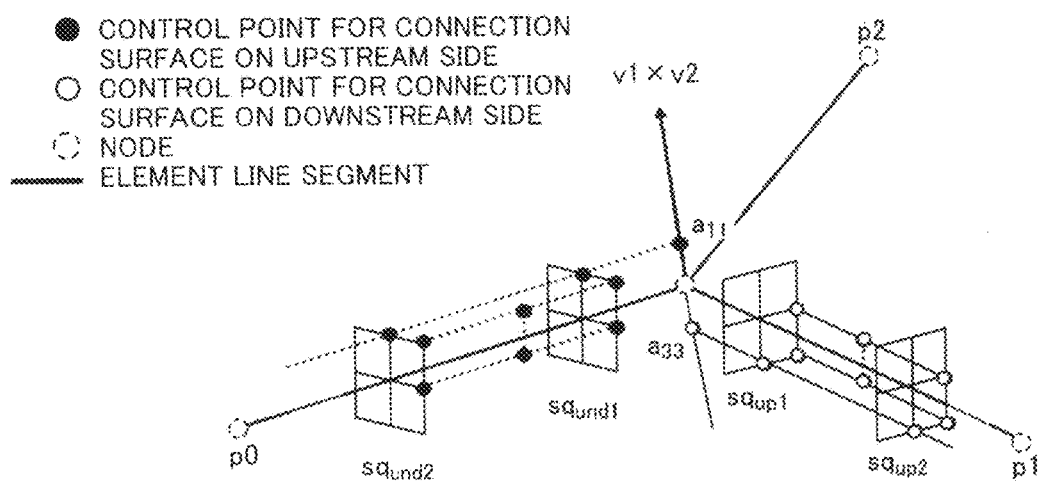
FIG. 14 illustrates an example of a combination of control points for connection surfaces.

The following describes how to obtain control point candidates and how to combine the control point candidates, with reference to FIGS. 13 and 14. FIG. 13 illustrates an example of combining control points for surfaces covering a joint. FIG. 14 illustrates an example of a combination of control points for connection surfaces.

First, as node-based control point candidates, two points ($a_{11}$ and $a_{33}$) on the straight line orthogonal to the plane A and a point ($a_{22}$) at the joint portion are set. Since there are three joints at a single branch point, three points at the respective joint portions are set for the single branch point.

The coronary circulation model 30 is generated with, for example, the Constructive Constrained Optimization (CCO) algorithm. This CCO algorithm sets a flow distribution in the shape of an organ, and gives pressures at vertices and distal points of blood vessels having a tree structure. Then, the CCO algorithm generates blood vessel elements from the distal points, and connects a blood vessel element to another and shifts a connection point to another such that the total capacity of blood vessels is the minimum, according to the Poiseuille's flow law. With respect to the branching of the artery blood vessels, according to the CCO algorithm, every upstream blood vessel element branches into only two downstream blood vessel elements. Therefore, there are three joints at each branch point. The curved surface information generation unit 130 sets the following points as element-based control point candidates.

Points that are away by respective distances $m_0$ and $u_0$ from a branch point are set on an element line segment connecting the nodes at both ends of each of three blood vessel elements connected to each other at the branch point. Then, the curved surface information generation unit 130 generates squares which have the points set on the three element line segments as their centers, in planes orthogonal to the element line segments. Each side of a generated square has the same length as the diameter of the blood vessel element having the corresponding element line segment. As a result, two squares are generated for each of three element line segments extending from the branch point, and thus six squares are generated around the branch point. The curved surface information generation unit 130 gives identifiers $sq_{up1}$ and $sq_{up2}$ to the squares set on the downstream side of the branch point, in order from the upstream side. The curved surface information generation unit 130 also gives identifiers $sq_{und1}$ and $sq_{und2}$ to the squares set on the upstream side of the branch point, in order from the downstream side. Then, the curved surface information generation unit 130 sets 48 points: the vertices and middle points of the sides of the six squares generated around the branch point, as element-based control point candidates.

The following describes how to combine obtained control points (see FIG. 13). One of the NURBS surfaces at a joint portion is considered. The control points $a_{11}$ and $a_{33}$ are common among all the NURBS surfaces at the joint portion. The control point $a_{22}$ is uniquely determined according to a surface of attention. As the remaining six points, three points closer to the control point $a_{22}$ on the upstream side are selected in the squares $sq_{und1}$ and $sq_{und2}$, and three points closer to the control point $a_{22}$ on the downstream side are selected in the square $sq_{up1}$. The following describes how to select three points closer to the control point $a_{22}$.

The eight points in a square are given numbers in the right screw direction of a vector from the upstream to the downstream of an element. At this time, a point on $l_1$ is set as the start point. Thereby, with regard to a certain blood vessel element, there are two combinations of three point candidates: the second, third and fourth points; and the sixth, seventh, and eight points. The coordinates of the third and seventh points are compared with the coordinates of the control point $a_{22}$, and three points including one of these points, whichever is closer to the control point $a_{22}$, are set as control points. With the joint portion between downstream elements, control points are arranged, taking one element as an upstream element.

The following describes a combination of control points for connection surfaces (see FIG. 14). Using only control points in the squares $sq_{up1}$ and $sq_{up2}$ and control points $a_{11}$ and $a_{33}$ are insufficient as control points to be used for connection surfaces. Therefore, the curved surface information generation unit 130 obtains a middle point between the second control points of the two individual squares $sq_{up1}$ and $sq_{up2}$, as a control point. In addition, the curved surface information generation unit 130 obtains a middle point between the third control points of the two individual squares $sq_{up1}$ and $sq_{up2}$, as a control point. As a result, the nine control points are obtained for defining connection surfaces.

Similarly, the curved surface information generation unit 130 obtains middle points between the same-ordered control points of the two individual squares $sq_{und1}$ and $sq_{und2}$, as control points. This complements control points to be used for the connection surfaces.

The following describes a procedure for generating a surface covering a branch point when the coronary circulation model 30 is displayed. In summary, control point candidates that are intermediate data are generated from the coronary circulation model 30, and control point data is generated from the intermediate data. Then, the coronary circulation, which is the final output data, is displayed. The intermediate data is generated on the basis of nodes and elements. At this time, element-based control point candidates are obtained using the coordinates of a node-based control point candidate. Therefore, a process of obtaining node-based control point candidates is performed first.

Figure 15:
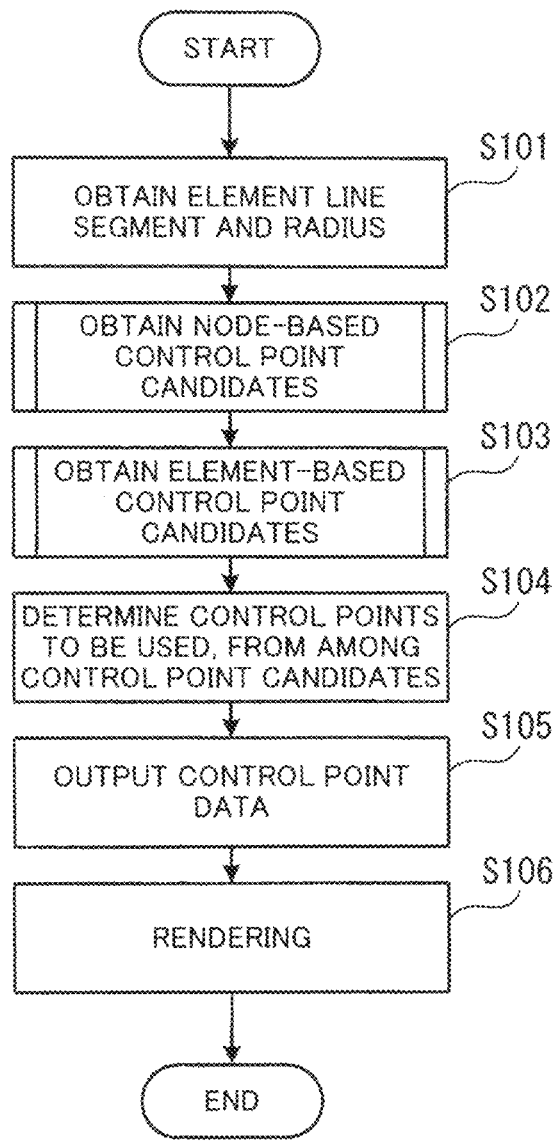
FIG. 15 is a flowchart illustrating an example of a procedure for a process of generating a surface that covers a branch point.

FIG. 15 is a flowchart illustrating an example of a procedure for a process of generating a surface that covers a branch point.

(Step S101) The branch point detection unit 120 obtains the element line segment and radius of a blood vessel element. For example, the branch point detection unit 120 obtains the nodes at both ends and the radius of a blood vessel element from the blood vessel element information table 112. Then, the branch point detection unit 120 obtains the coordinates of the nodes at both ends of the blood vessel element. A line segment connecting the obtained coordinates is taken as an element line segment.

(Step S102) The branch point detection unit 120 and the curved surface information generation unit 130 obtain node-based control point coordinates at the branch point in collaboration with each other. This process will be described in detail later (refer to FIG. 16).

(Step S103) The curved surface information generation unit 130 obtains element-based control point coordinates. This process will be described in detail later (refer to FIG. 17).

(Step S104) The curved surface information generation unit 130 determines appropriate control points for use in defining NURBS surfaces from among the control point candidates. The appropriate control points for use in defining NURBS surfaces have been described with reference to FIGS. 6 to 14.

(Step S105) The curved surface information generation unit 130 outputs control point data.

(Step S106) The model display unit 140 renders the NURBS surfaces on the basis of the control point data output from the curved surface information generation unit 130.

The following describes how to obtain node-based control point candidates.

Figure 16:
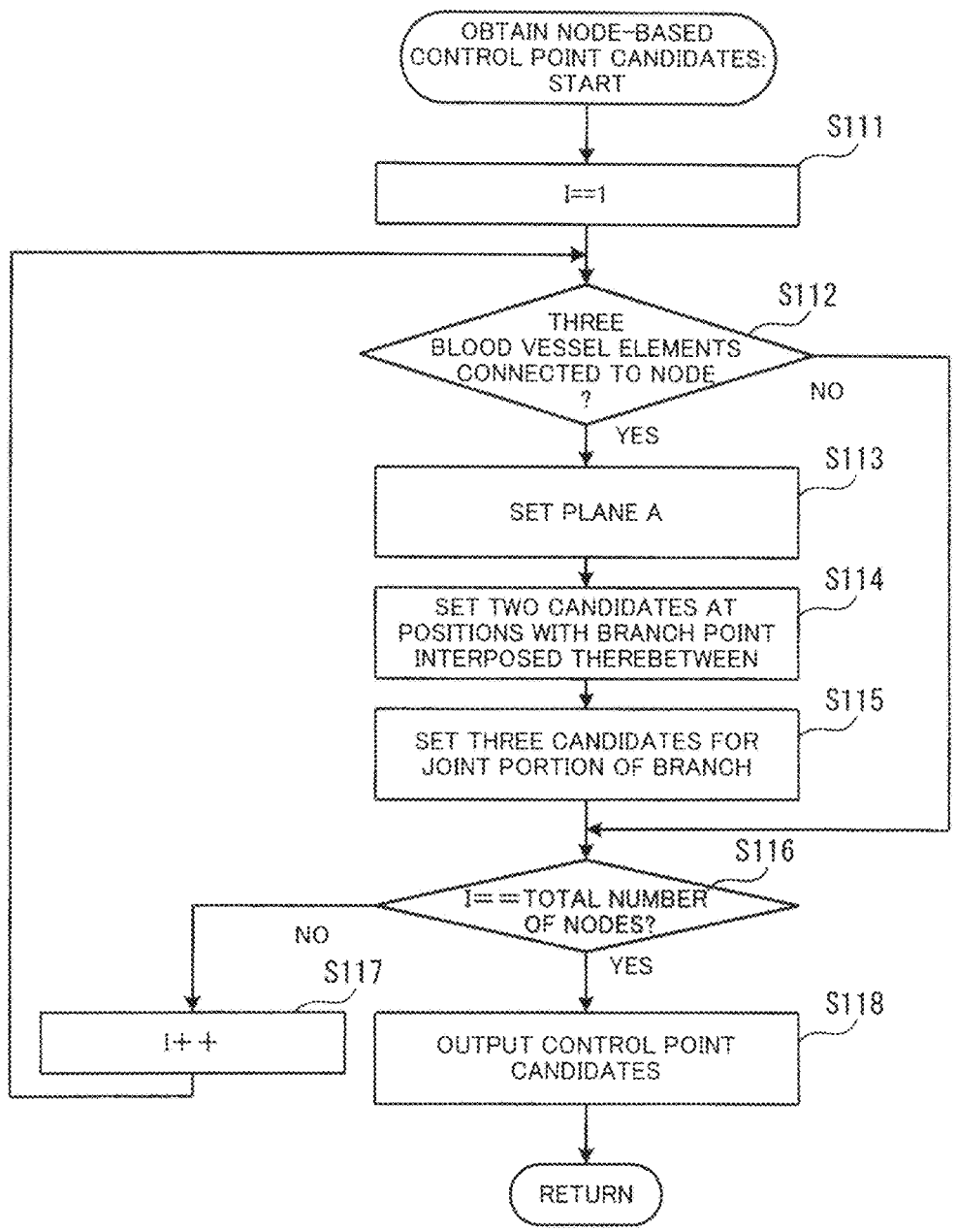
FIG. 16 is a flowchart illustrating an example of a procedure for a process of obtaining node-based control point candidates.

FIG. 16 is a flowchart illustrating an example of a procedure for a process of obtaining node-based control point candidates.

(Step S111) The branch point detection unit 120 sets a variable I specifying a node number to "1".

(Step S112) The branch point detection unit 120 determines whether there are three blood vessel elements connected to the I-th node or not. For example, if three nodes are registered in a node field corresponding to the node number I in the blood vessel element information table 112, the branch point detection unit 120 determines that there are three blood vessel elements connected to the node. If three blood vessel elements are connected, the I-th node is determined as a branch point, and then the process proceeds to step S113. If three blood vessel elements are not connected, the process proceeds to step S116.

(Step S113) The curved surface information generation unit 130 sets a plane A. For example, the curved surface information generation unit 130 generates, as the plane A, a plane including nodes of the three element line segments having the opposite nodes connected to the I-th node.

(Step S114) The curved surface information generation unit 130 sets two points with the branch point interposed therebetween, as control point candidates. For example, the curved surface information generation unit 130 defines a straight line that passes through the branch point and is orthogonal to the plane A. Then, the curved surface information generation unit 130 sets two points away by a distance r from the branch point on the defined straight line, as control point candidates.

(Step S115) The curved surface information generation unit 130 sets control point candidates for three joint portions at the branch point. In this case, three candidates are set for the three joints.

(Step S116) The curved surface information generation unit 130 determines whether the value of the variable I reaches the total number of nodes or not. If the total number of nodes is not reached, the process proceeds to step S117. Otherwise, the process proceeds to step S118.

(Step S117) The curved surface information generation unit 130 increments the variable I (by one), and the process proceeds to step S112.

(Step S118) The curved surface information generation unit 130 outputs the control point candidates.

As described above, the node-based control point candidates are output. The following describes how to obtain element-based control point candidates.

Figure 17:
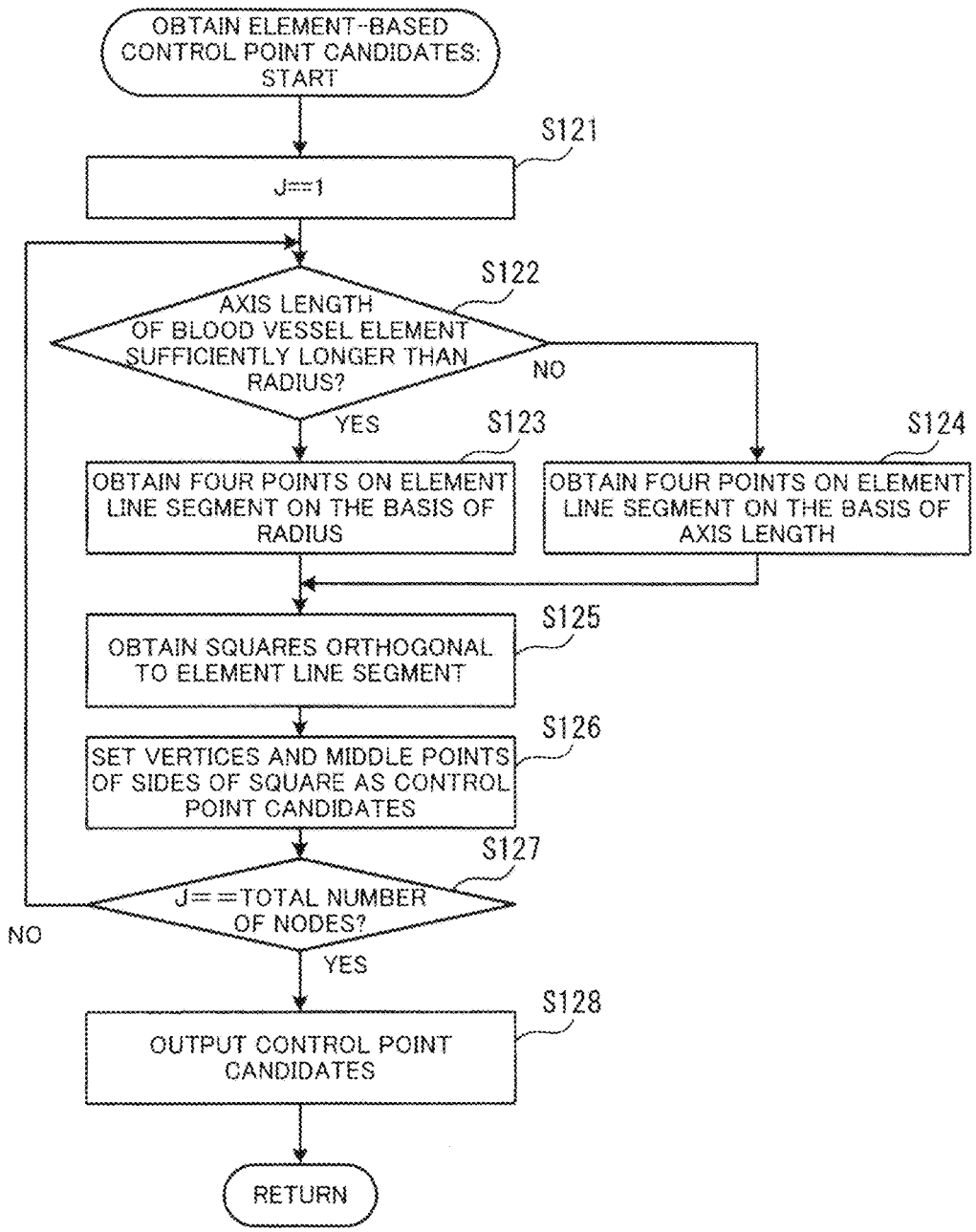
FIG. 17 is a flowchart illustrating an example of a procedure for a process of obtaining element-based control point candidates.

FIG. 17 is a flowchart illustrating an example of a procedure for a process of obtaining element-based control point candidates.

(Step S121) The curved surface information generation unit 130 sets a variable J specifying an element number of a blood vessel element to "1".

(Step S122) The curved surface information generation unit 130 determines whether the axis length $l_J$ ($l_J$ is a positive real number) of the J-th blood vessel element is sufficiently longer than the radius $r_J$ ($r_J$ is a positive real number). For example, the curved surface information generation unit 130 determines that the axis length is sufficiently long if the axis length is longer than a value obtained by multiplying the radius by a predetermined value. If the axis length is sufficiently long, the process proceeds to step S123. Otherwise, the process proceeds to step S124.

(Step S123) The curved surface information generation unit 130 obtains four points on the element line segment on the basis of the radius. For example, the curved surface information generation unit 130 obtains four points in total: two points away by $2r_J$ and $4r_J$ from the start point and two points away by $2r_J$ and $4r_J$ from the end point. Then, the process proceeds to step S125.

(Step S124) The curved surface information generation unit 130 obtains four points on the element line segment on the basis of the axis length. For example, the curved surface information generation unit 130 obtains four points in total: two points away by $l_J/5$ and $(2l_J)/5$ from the start point and two points away by $l_J/5$ and $(2l_J)/5$ from the end point.

(Step S125) The curved surface information generation unit 130 obtains squares with each side of $2r_J$ in length and with one of the obtained four points as a center, in planes orthogonal to the element line segment.

(Step S126) The curved surface information generation unit 130 sets eight points: the vertices and middle points of the sides of each obtained square, as control point candidates.

(Step S127) The curved surface information generation unit 130 determines whether the value of the variable J reaches the total number of nodes or not. If the total number of nodes is not reached, the process proceeds to step S122. Otherwise, the process proceeds to step S128.

(Step S128) The curved surface information generation unit 130 outputs the control point candidates.

As described above, control point candidates are set, and control points for surfaces covering the joint portions and connection surfaces are determined from among the candidates. After the control points are determined, surfaces for covering the branch point are generated on the basis of the control points, so that the blood vessel elements at the branch point are displayed with smooth curved surfaces.

Figure 18:
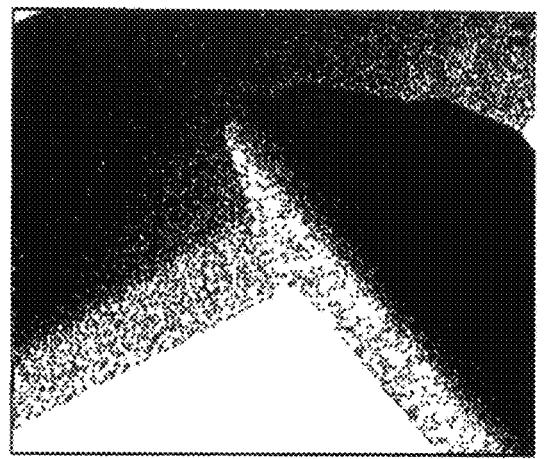
FIG. 18 illustrates an example of displaying a portion around a branch point.
Figure 18:
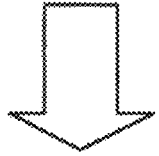
Figure 18:
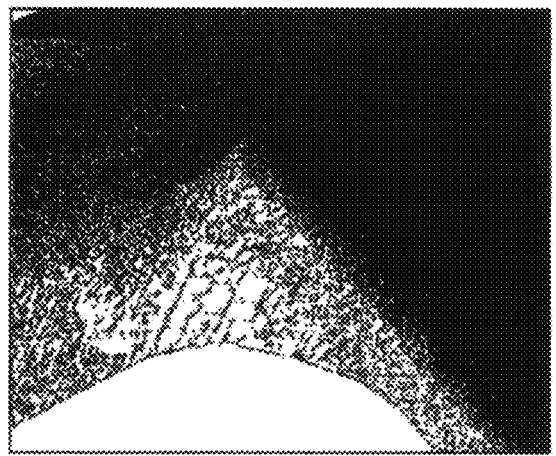

FIG. 18 illustrates an example of displaying a portion around a branch point. In FIG. 18, the upper drawing illustrates an image obtained before surfaces for covering the branch point are added, and the lower drawing illustrates an image obtained with surfaces covering the branch point added. As is seen in FIG. 18, in the image obtained before surfaces for covering the branch point are added, a joint between blood vessel elements is not smooth. On the other hand, by adding surfaces covering the branch point, the portion where the blood vessel branches is displayed with a smooth curved line.

As described above, according to the second embodiment, blood vessels forming a coronary circulation are joined smoothly, and the coronary circulation is displayed without any biological strangeness.

In this connection, in the second embodiment, it is possible to adjust the coordinates of control points to be arranged, using a parameter.

Figure 19:
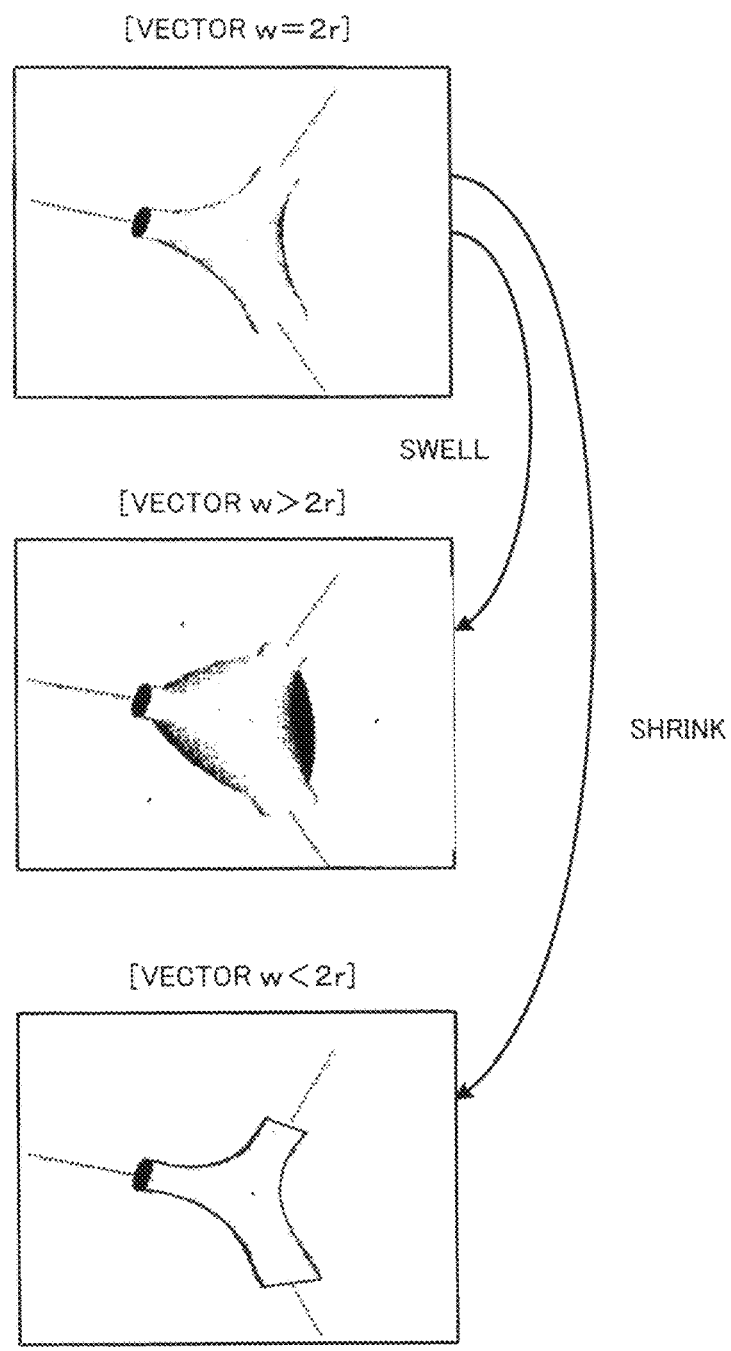
FIG. 19 illustrates differences in the shape of a surface covering a branch point between parameter values.

FIG. 19 illustrates differences in the shape of a surface covering a branch point between parameter values. The parameter to be used is a coefficient by which a vector for obtaining control points to be arranged in a joint portion among node-based control points is multiplied. The surface may rise or drop, depending on the parameter value. For example, if the length of the vector w is set longer than 2r, the blood vessel at the branch point swells. If the length of the vector w is set shorter than 2r, the blood vessel at the joint portion of the branch point greatly shrinks.

Further, a technique described in the second embodiment is a technique for biologically displaying a result of simulating a biological entity, and has the premise that entered data has the characteristics of the biological entity. There is no guarantee that branch angles are equal.

Figure 20:
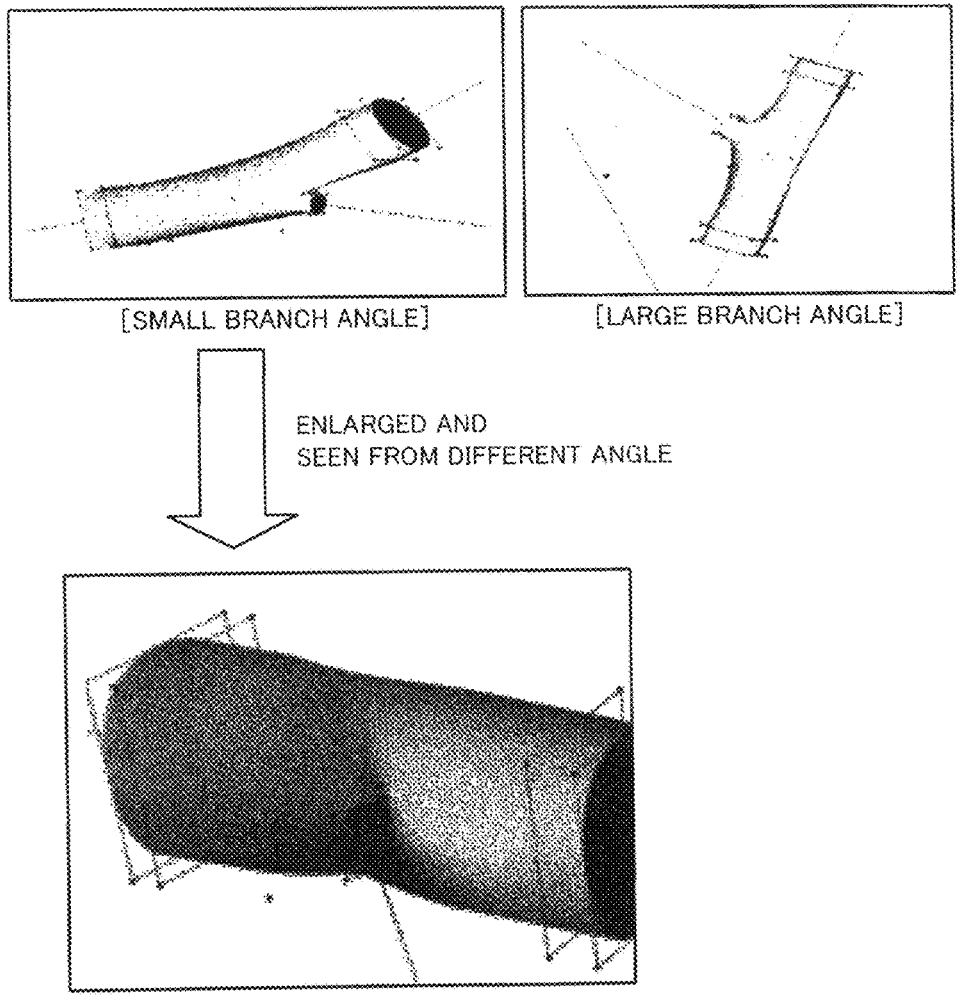
FIG. 20 illustrates an example of displaying branch points each having a small or a large branch angle.

FIG. 20 illustrates an example of displaying branch points each having a small or a large branch angle. In FIG. 20, the upper left drawing illustrates an example of displaying a portion with a small branch angle. The lower drawing illustrates an example of an enlarged display of the same branch portion as the upper left drawing, seen from a different angle. As is seen in FIG. 20, even if the branch angle is small, the blood vessels are connected smoothly at the branch portion. The upper right drawing in FIG. 20 illustrates an example of displaying a portion with a large branch angle. As is seen in FIG. 20, even if the branch angle is large, the blood vessels are connected smoothly at the branch portion.

The above description uses the example of displaying a branch point smoothly where three blood vessel elements are connected to each other. In addition, a branch point where four or more blood vessel elements are connected to each other may be displayed as a smooth surface in the same way. Moreover, even when two blood vessel elements are connected to each other, the connection portion may be displayed as a smooth surface in the same way.

The foregoing is considered as illustrative only of the embodiments. Each constitutional element in the embodiments may be replaced by any other element having equivalent functions. Further, any other configuration or step may be added thereto. Still further, two or more configurations (features) in the embodiments may be combined to provide the disclosed techniques.

According to one aspect, it is possible to display connection portions between a plurality of elements such that they look natural.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

What is claimed is:

1. A shape data generation apparatus, comprising:
a processor configured to execute a process including:
  detecting a connection point where two or more elements are connected to each other, based on positions of both ends of each of a plurality of elements, with reference to model information indicating thicknesses and the positions of the both ends of the plurality of elements each having a cylindrical surface; and
  generating a curved surface, for collectively covering connecting ends of the two or more elements, based on the thicknesses and the positions of the both ends of the two or more elements connected at the connection point, wherein
  the generating the curved surface includes:
    defining, when a length of an element is longer than a value obtained by multiplying a radius of the element by a predetermine value, a plane orthogonal to a line segment connecting both ends of the element, at a first position away by a distance that is a predetermined times longer than the radius from the connection point, on the line segment;
    defining, when the length of the element is shorter than or equal to the value, a plane orthogonal to the line segment connecting the both ends of the element, at a second position away by a distance that is shorter than the length of the element from the connection point, on the line segment; and
    setting control points for defining a shape of the curved surface, on the defined plane.

2. The shape data generation apparatus according to claim 1, wherein the generating the curved surface further includes generating, at the connection point where three elements are connected to each other, a first curved surface covering a joint portion between a first element and a second element, a second curved surface covering a joint portion between the first element and a third element, a third curved surface covering a joint portion between the second element and the third element, and one or more curved surfaces covering gaps between the first to third curved surfaces.

3. The shape data generation apparatus according to claim 2, wherein the generating the curved surface further includes:
  setting one or more control points for defining a first shape of the first curved surface, on each of a surface of the first element and a surface of the second element;
  setting one or more control points for defining a second shape of the second curved surface, on each of a surface of the first element and a surface of the third element; and
  setting one or more control points for defining a third shape of the third curved surface, on each of the surface of the second element and the surface of the third element.

4. The shape data generation apparatus according to claim 2, wherein the generating the curved surface further includes:
  obtaining a radius of a thickest element among the two or more elements connected at the connection point;
  obtaining two points that are away by a distance equal to the obtained radius from the connection point and are symmetrical about the connection point; and
  using the obtained two points as control points for all the first to third curved surfaces.

5. The shape data generation apparatus according to claim 2, wherein the generating the curved surface further includes generating, as one or more curved surfaces covering the gaps, curved surfaces each sharing one or more control points with one of the first to third curved surfaces and having control points arranged on the one of the first to third curved surfaces.

6. A shape data generation method, comprising:
  detecting, by a processor, a connection point where two or more elements are connected to each other, based on positions of both ends of each of a plurality of elements, with reference to model information indicating thicknesses and the positions of the both ends of the plurality of elements each having a cylindrical surface; and
  generating, by the processor, a curved surface for collectively covering connecting ends of the two or more elements, based on the thicknesses and the positions of the both ends of the two or more elements connected at the connection point, wherein the generating the curved surface includes:

defining, when a length of an element is longer than a value obtained by multiplying a radius of the element by a predetermine value, a plane orthogonal to a line segment connecting both ends of the element, at a first position away by a distance that is a predetermined times longer than the radius from the connection point, on the line segment;

defining, when the length of the element is shorter than or equal to the value, a plane orthogonal to the line segment connecting the both ends of the element, at a second position away by a distance that is shorter than the length of the element from the connection point, on the line segment; and setting control points for defining a shape of the curved surface, on the defined plane.

7. A non-transitory computer-readable storage medium storing therein a computer program that causes a computer to execute a process comprising:

detecting a connection point where two or more elements are connected to each other, based on positions of both ends of each of a plurality of elements, with reference to model information indicating thicknesses and the positions of the both ends of the plurality of elements each having a cylindrical surface, and generating a curved surface for collectively covering connecting ends of the two or more elements, based on the thicknesses and the positions of the both ends of the two or more elements connected at the connection point, wherein the generating the curved surface includes:

defining, when a length of an element is longer than a value obtained by multiplying a radius of the element by a predetermine value, a plane orthogonal to a line segment connecting both ends of the element, at a first position away by a distance that is a predetermined times longer than the radius from the connection point, on the line segment;

defining, when the length of the element is shorter than or equal to the value, a plane orthogonal to the line segment connecting the both ends of the element, at a second position away by a distance that is shorter than the length of the element from the connection point, on the line segment; and setting control points for defining a shave of the curved surface, on the defined plane.

* * * * *